(12) United States Patent
Grass et al.

(10) Patent No.: US 7,839,967 B2
(45) Date of Patent: Nov. 23, 2010

(54) ELECTRON COMPUTER TOMOGRAPHY METHOD AND ELECTRON COMPUTER TOMOGRAPH

(75) Inventors: Michael Grass, Buchholz in der Nordheide (DE); Thomas Koehler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 409 days.

(21) Appl. No.: 11/721,165

(22) PCT Filed: Dec. 8, 2005

(86) PCT No.: PCT/IB2005/054118

§ 371 (c)(1),
(2), (4) Date: Jun. 8, 2007

(87) PCT Pub. No.: WO2006/064419

PCT Pub. Date: Jun. 22, 2006

(65) Prior Publication Data

US 2009/0238326 A1    Sep. 24, 2009

(30) Foreign Application Priority Data

Dec. 17, 2004    (EP)    ................... 04106679

(51) Int. Cl.
*G01N 23/00* (2006.01)
(52) U.S. Cl. .......................................... 378/12; 378/10
(58) Field of Classification Search ...................... 378/4, 378/8, 9, 10, 12, 20
See application file for complete search history.

(56) References Cited

U.S. PATENT DOCUMENTS

| | | | |
|---|---|---|---|
| 5,654,995 A | 8/1997 | Flohr | |
| 6,490,333 B1 | 12/2002 | Hsieh | |
| 2002/0025017 A1* | 2/2002 | Stergiopoulos et al. | ........ 378/8 |
| 2004/0092811 A1 | 5/2004 | Hill | |
| 2004/0120450 A1 | 6/2004 | Flohr et al. | |
| 2004/0136490 A1 | 7/2004 | Edic et al. | |
| 2004/0136501 A1* | 7/2004 | Boyd et al. | ................. 378/210 |
| 2004/0208276 A1 | 10/2004 | Kaufman | |

OTHER PUBLICATIONS

Besson, G. M., et al.; Partial Scan Weighting Algorithms with Applications to Arbitrary Pitch Selection in Multislice CT and Cardiac CT Sector Reconstruction; 2001; IEEE Nuclear Symposium Conf. Record; vol. 2; pp. 15-94-100.

Hsieh, J.; Reconstruction Algorithm for Single Circular Orbit Cone Beam Scans; 2002; IEEE Int. Symposium on Biomedical Imaging; pp. 836-838.

* cited by examiner

*Primary Examiner*—Hoon Song

(57) ABSTRACT

There is provided an electron computer tomography method for recording a moving object (27), in which an electron beam is deflected onto an anode arc (14) in order to generate X-ray radiation which passes through an object (27) and is picked up by a detector device (28), wherein the X-ray radiation leaves the anode arc (14) in the form of a fan-shaped beam having a source trajectory (40) in the form of a circle segment around the object (27) and the starting point (41) of the source trajectory (40) can be changed. Also provided is an electron computer tomograph for recording a moving object (27), comprising an electron gun (8), a focusing coil (12), a curvature coil (16), an anode arc (14) for generating an X-ray beam by being struck by an electron beam of the electron gun (8), and a detector device (28) for detecting the X-ray radiation transmitted through a volume (26), said X-ray radiation having a source trajectory (40) in the form of a circle segment at the anode arc (14) and a variable starting point (41) of the source trajectory (40).

20 Claims, 2 Drawing Sheets

ELECTRON COMPUTER TOMOGRAPHY METHOD AND ELECTRON COMPUTER TOMOGRAPH

The invention relates to an electron computer tomography method as claimed in the preamble of claim 1 and to an electron computer tomograph as claimed in the preamble of claim 11.

In the field of computer tomography, various methods are used industrially. Particularly when short recording times or scanning times are desired, use is made of Electron Beam Computer Tomographs (EBCT). These do not require any mechanical movements of the radiation source since the radiation source in this case is not moved around the object but rather a deflected electron beam strikes an anode arc, also known as a target, of the X-ray tube, is deflected along the anode arc, and in this way the X-ray radiation generated at the target moves toward the object to be examined. In particular, a high dose power of the X-ray radiation is achieved as a prerequisite for short recording times or scanning times. Usually, the electron beam migrates along a complete anode arc by 360° around the object, and the electron computer tomograph records data relating to the attenuation values of the X-ray radiation by means of a detector device which is usually stationary and is arranged in an arc along the object to be examined. These data, which are recorded from different positions around the object, are then reconstructed to form an image.

It is an object of the invention to provide short recording times with a high image quality in an electron computer tomograph.

According to the invention, this object is achieved by the features of claim 1 and claim 11.

There is provided an electron computer tomography method for recording a moving object, in which an electron beam is deflected onto an anode arc in order to generate X-ray radiation which passes through an object and is picked up by a detector device, wherein the X-ray radiation leaves the anode arc in the form of a fan-shaped beam having a source trajectory in the form of a circle segment around the object and the starting point of the source trajectory can be changed. Also provided is an electron computer tomograph for recording a moving object, comprising an electron gun, a focusing coil, a curvature coil, an anode arc for generating an X-ray beam by being struck by an electron beam of the electron gun, and a detector device for detecting the X-ray radiation transmitted through a volume, said X-ray radiation having a source trajectory in the form of a circle segment at the anode arc and a variable starting point of the source trajectory. The object can be reconstructed to form an image by using data which are recorded starting from different starting points of the source trajectory. By virtue of the present invention, a stable reconstruction of the image with a high image quality is achieved even though, on account of the generally shorter source trajectory, not all the data obtained from the radiation passing through the object are used for the reconstruction.

Particular embodiments of the invention are described in the dependent claims.

In one embodiment, the starting point of the source trajectory can be changed as a function of a movement state of the object. In particular, the starting point of the source trajectory is selected as a function of a movement state of the object at a point in time with as little movement of the object as possible, so that the fan-shaped beam coming from the starting point precisely covers the object in a volume and no parts of the object are missed by the fan-shaped beam on account of the movement of the object. Consequently, few image artifacts arise on account of movements of the object.

In another embodiment, the starting point of the source trajectory can be determined on the basis of results of an electrocardiogram of the object. In order to determine the movement state, the phase of the object is recorded for example by means of an electrocardiograph. The computer tomograph then controls the starting point of the source trajectory on the basis of the results from the electrocardiograph.

Furthermore, the starting point of the source trajectory can be changed as a function of the vertical position of the object. If the vertical position of the object is changed, by virtue of height adjustment of the patient table, the object may move out of the range of the fan-shaped beam and the image reconstruction may then become unstable. For this reason, in the event of a change in the vertical position of the object, the starting point of the source trajectory at the anode arc is changed in such a manner that the entire object, for example a heart, is covered by the fan-shaped beam coming from the anode arc.

Moreover, a filtered back-projection is carried out in order to reconstruct the image, wherein it has been found that a stable reconstruction with good results can be achieved by means of this reconstruction method even though a shorter source trajectory compared to the prior art is selected which leads to less recorded data than is customary.

The invention will be further described with reference to examples of embodiments shown in the drawings to which, however, the invention is not restricted.

Figure 1:
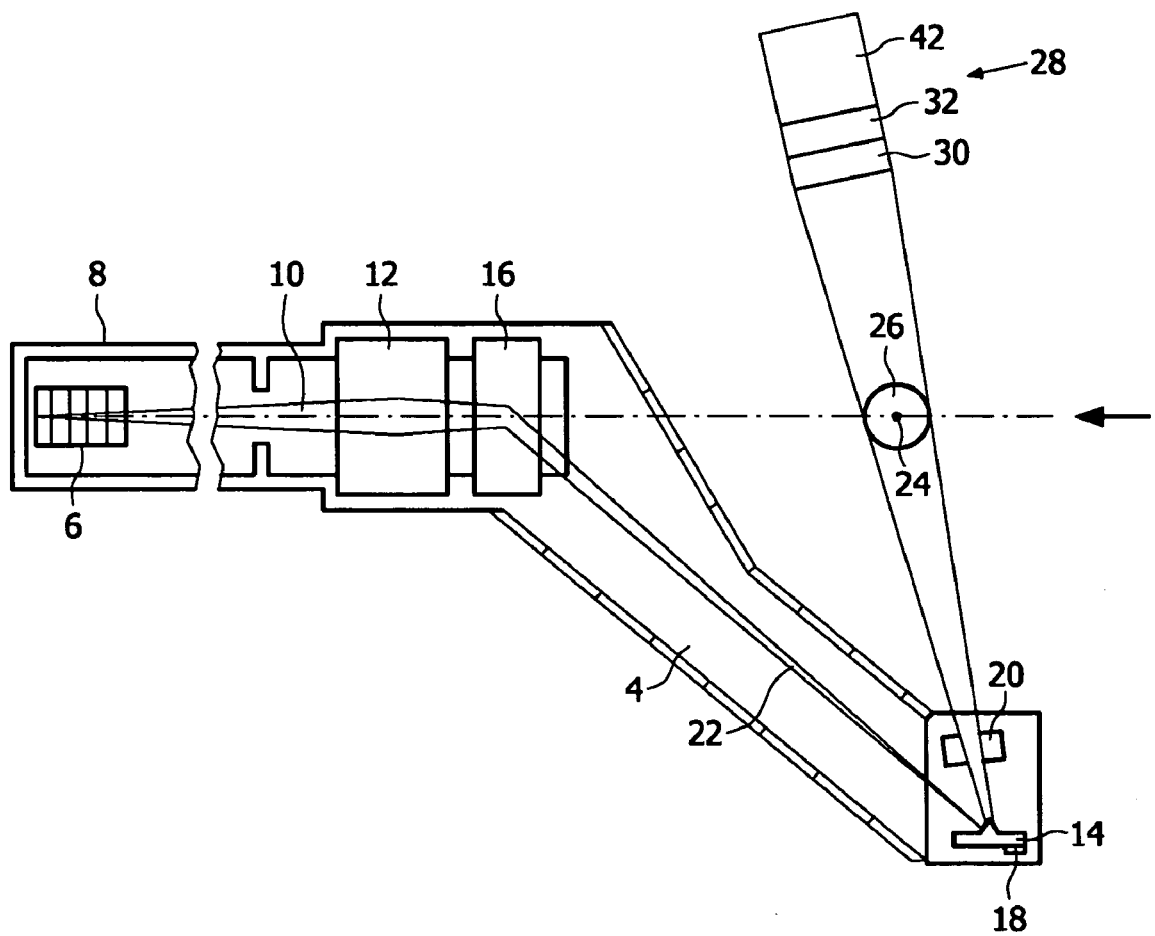
FIG. 1 shows a schematic side view of part of an electron beam computer tomograph.

FIG. 1 shows a schematic view of an example of embodiment of part of an electron beam computer tomograph. The figure shows an electron beam tube with a vacuum chamber 4 which has an electron gun 6 at its cylindrical end 8. The electron gun 6 emits an axial electron beam 10 along the cylindrical portion. Focusing coils 12 and curvature coils 16 are provided for focusing the electron beam 10 and for controlling the electron beam 10 along an anode arc 14 or target ring, only part of which is shown. The curvature coils 16 are controlled by a suitable controller in such a manner that the electron beam 10 can rapidly be pivoted along a path or trajectory along the anode arc 16. The trajectory and the anode arc 14 consequently have the same profile.

The anode arc 14 is made of a suitable material, for example tungsten, so that an X-ray beam is produced from the point at which the electron beam 22 strikes the anode arc 14. The center line of the anode arc 14 as the source of the emitted X-ray radiation is also referred to as the source trajectory 40. The source trajectory 40 is not planar but rather is curved in a manner corresponding to the profile of the anode arc 14, as described below, but does not have a full circular path like the latter.

A suitable cooling coil 18 may be fixed to the anode arc 14, said cooling coil being designed to cool the anode arc 14. The electron beam computer tomograph has a specific central point, the isocenter 24. The orientation of the electron beam 22 and of the anode arc 14 is such that the axis of the fan-shaped beam of X-ray radiation which comes from a point on the anode arc 14 points toward the isocenter 24.

Moreover, the electron beam computer tomograph has a detector device 28 which is arranged opposite the anode arc 14. FIG. 1 shows only a cross section of the detector device 28. The electron beam computer tomograph records perpendicular projections of the fan-shaped beam of a given volume 26 around the isocenter 24, in which an object 27 to be examined is located. The volume 26 of interest is large enough to include the object 27, for example a human heart.

Reference 20 denotes a collimator which is arranged close to the anode arc 14 and between the anode arc 14 and the detector device 28. The collimator 20 filters X-rays which are emitted from the anode arc 14 and cannot strike the detector device 28.

The detector device 28 is formed of a large number of detector modules 32. Each detector module 32 has a flat rectangular pick-up area which is covered by a grid 30 in order to prevent scattered radiation. The detector electronics may be arranged behind the chamber 42 behind the pick-up area with respect to the impinging X-ray radiation.

The pick-up area of the detector device 28 is oriented toward the anode arc 14. A straight line which starts at the center point of the pick-up area and runs through the isocenter 24 meets the anode arc 14. The grid 30 for preventing scattered radiation is focused on this meeting point on the anode arc 14.

The detector modules 32 are arranged side to side such that their pick-up areas form a strip. The center line of the strip is referred to as the detector trajectory. The detector trajectory is not planar and is curved in a manner corresponding to the detector device 28. In particular, any straight line which starts from a point on the source trajectory 30 and passes through the isocenter 24 meets the detector trajectory. The detector trajectory is therefore a mirror image of the source trajectory 40, reflected at the isocenter 24.

The values obtained in this way by the detector device 28 are then subjected to a reconstruction method, or reconstruction for short, in order to obtain an image of the object 27. In particular, filtered back-projection is used for this purpose. Filtered back-projection has the advantage that it requires a low calculation complexity compared to other reconstruction methods, leads to images of very good quality, permits a reconstruction of any sub-regions of the examination area or volume 26 and allows simultaneous processing of different projections or measured values, that is to say parallel processing of measured values.

Filtered back-projection can be described by the formula $$\tilde{\mu} = \frac{1}{N} \sum_i B_i F_i p_i \quad (1)$$

wherein $\tilde{\mu}$ is the reconstructed image and N is the number of radiation source positions, striking points on the anode arc 14 from which measured values or projections that are used for reconstruction are acquired by the detector device 28.

Furthermore, $F_i$ is the filter operator which is assigned to the radiation source position or to the projection direction of a projection $p_i$.

A back-projection operator $B_i$ projects a projection along rays of the $i^{th}$ radiation source position back into the examination area.

Figure 2:
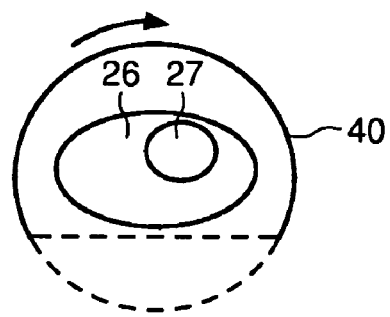
FIG. 2 shows a path of an X-ray beam around a volume for recording an examination object.

FIG. 2 shows a full circular path around the volume 26, also referred to as the field of view (FOV), seen from the direction of the arrow in FIG. 1, wherein the source trajectory 40 is shown by a continuous circular line and regions of the path on the anode arc 14 outside the source trajectory 40 are shown in dashed line. The source trajectory 40 runs along the anode arc 14. The electron beam consequently strikes the anode arc 14 at the continuous line and generates X-ray radiation. The starting point 41 and the end point 42 of the source trajectory 40, from which X-ray radiation is emitted, are connected by a dashed line for illustrative purposes. The curved arrow in FIG. 2 shows the direction in which the electron beam migrates along the anode arc 14 and the source trajectory 40. The fan-shaped X-ray beam, which is produced by striking the anode arc 14 with the electron beam, comes from the anode arc 14 and always covers the volume 26. As already mentioned, the electron beam migrates along the source trajectory 40 and emits a fan-shaped X-ray beam always in the direction of the volume 26. The object 27 to be examined, in this case the heart, is located in the volume 26 and is accordingly always covered by the X-ray beam. The source trajectory 40, which is shown here as a continuous line, in this case takes up 180° of the circular path around the volume 26 plus the fan angle of the X-ray beam, and together these amount to around 220° to 240°.

Figure 3:
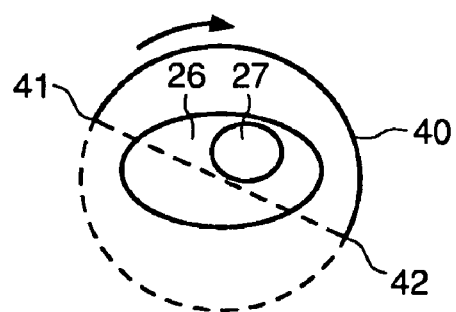
FIG. 3 shows an improved path of an X-ray beam around a volume for recording an examination object.

FIG. 3 shows a further path, around the volume 26, of the electron beam which strikes the anode arc 14. Unlike in FIG. 2, the source trajectory 40 here is shorter and takes up less length along the anode arc 14; the electron beam migrates a much shorter distance around the volume 26 than in FIG. 2. The source trajectory 40 in this case forms only a segment of a circle around the object 27. The circle segment is less than 180° of the circular path around the volume 26 plus the fan angle of the X-ray beam, less than about 220° to 240°. The starting point 41 of the electron beam is shifted to the right along the curved arrow compared to FIG. 2, and the end point 42 of the electron beam lies more or less at the same point as the end point 42 shown in FIG. 2. The starting point 41 and the end point 42 of the source trajectory 40, shown in the figure at the start and end of the continuous circular line, depend inter alia on the position of the object 27 within the volume 26. For example, the height of the patient table may be changed, wherein the patient and the object 27 are shifted in the vertical direction. It is possible in the process that the object 27 will leave the coverage area of the X-ray beam. In this case, the starting point 41 on the source trajectory 40 can be changed such that the object 27 is covered despite the vertical change in position and a smaller circular segment. If the object 27 is lowered downward, the starting point 41 of the X-ray beam therefore migrates to the left for example in the opposite direction to that of the curved arrow in FIG. 3, so that the X-ray beam covers the entire object 27. That starting point 41 is selected at which the X-ray beam fan from the starting point 41 of the source trajectory 40 to the detector device 28 just covers the edge of the object 27, as shown in FIGS. 2, 3 and 4 by the dashed straight lines between the starting points 41 and the end points 42.

Despite the smaller source trajectory 40, the object 27 which is located within the volume 26 is completely covered by the X-ray beam from any point on the anode arc 14, and a complete image of the object 27 is always picked up by the opposite detector device 28 from any point of the source trajectory 40. By virtue of the smaller source trajectory 40 compared to a full circular path, a higher temporal resolution can be achieved and measured values required for the reconstruction are recorded more quickly than when using longer source trajectories 40 having a full circular path or a path of more than 180° around the volume 26. The radiation dose on the object 27 is consequently reduced and critical movements of the object 27, for example heart movements, do not have such a great effect on the imaging, since the recording time or scanning time is reduced. According to current opinion, a stable two-dimensional reconstruction of an object 27 is possible only if all line integrals through the object 27 are measured. According to the present method, a stable reconstruction of the image is achieved if, as a prerequisite, each line which runs through the volume 26 intersects the circular path around the volume 26 in a non-tangential manner.

In particular, different movement states of the object 27 are compared with one another by comparing the images reconstructed from the measured data of the detector device 28. The measured data comprise different movement states or phases of the moving object 27. The reconstructed images are preferably slice images of the object 27, which are subjected to a comparison method in an associated computer device in order to determine the degree of similarity of the reconstructed images of the slices with one another. If there is a high degree of similarity of the images, then there is a similar movement state of the object 27; for example, if two images of slices of the object 27 are similar, the moving object 27 is in a similar movement state or phase of its movement in the two images. These similar images of slices which are determined by means of a comparison method are combined to form an overall image, so that a high coincidence of the movement states and consequently a high image quality is ensured.

Figure 4:
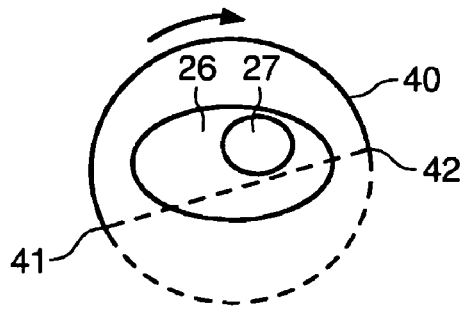
FIG. 4 shows a further improved path of an X-ray beam around a volume for recording an examination object.

FIG. 4 shows a further path or source trajectory 40, around the volume 26, of the electron beam which strikes the anode arc 14, in a manner similar to FIG. 3. Once again, the electron beam of the electron gun 6 strikes only a segment of the circle around the volume 26, shown in continuous line. Starting point 41 and end point 42 of the electron beam differ from those in FIG. 3; the starting point 41 of the electron beam is located for example at the starting point 41 shown in FIG. 2 and the end point 42 is located in a manner such that it has been shifted to the right along the curved arrow compared to FIG. 3, on the anode arc 14. It is shown that starting point 41 and end point 42 of the striking points of the electrode beam on the anode arc 40 are variable. These may be set in a manner dependent on the position of the object 27 in the volume 26.

Moreover, a phase of the object 27 can be determined in which there is little intrinsic movement of the object 27. For this purpose, the intrinsic movement of the object 27 is determined, for example by recording using an electrocardiogram or a sensor and selecting phases with little intrinsic movement of the object 27. The sensor for recording the heart movements comprises an ultrasound device or a phonocardiography device. The recording of the object 27 is started at this selected phase with little movement of the object 27 by directing the electron beam 22 onto the anode arc 14. A phase of the object 27 which has little movement may be, in the example of a heart, the late diastole or end systole. Another possibility for obtaining a phase with little intrinsic movement consists in recording all the phases of the movement independently of the movement state of the object 27, using the detector device 28. Each slice of the object 27 is recorded in n different phases of the movement. From the recorded data, images are reconstructed for each of the n different phases and those images of the slices which have the fewest movement artifacts are selected by the computer device of the electron computer tomograph. The phase in which the littlest movement occurs is thus selected from the n different phases.

For the purpose of obtaining a three-dimensional image, a number of slice images are recorded and reconstructed in the described manner. For a high image quality, slice images with a similar phase or movement state are required. However, the movement phase of the object 27 is not constant; for example, the heartbeat continually changes its phase, so that recordings of the slice images with a different movement state are produced, and additively these lead to image distortions. Using an electrocardiograph, in order to prevent the image distortions in the three-dimensional image, the phase of the object 27 is recorded and the computer device of the electron computer tomograph serves to control, on the basis of the electrocardiogram, at which point on the anode arc 14 the starting point 41 of the source trajectory 40 is set for each slice image. For example, if the phase of the object 27 becomes shorter, when a movement state is reversed more quickly than expected, the computer device controls the curvature coils 16 of the electron computer tomograph in such a manner that the starting point 41 of the source trajectory 40 is shifted counter to the direction of the curved arrow and the recording accordingly starts earlier. In a corresponding manner, the end point 42 of the source trajectory 40 is shifted by the same length counter to the direction of the curved arrow. If, on the other hand, the phase of the object is increased, when a movement state of the object 27 is delayed, the computer device controls the curvature coils 16 of the electron computer tomograph in such a manner that the starting point 41 of the source trajectory 40 is shifted along the curved arrow and the recording accordingly starts later. In a corresponding manner, the end point 42 of the source trajectory 40 is shifted along the curved arrow by the same length. If, for example, the phase of the object 27 becomes shorter, a movement state of the object 27 with little movement which is to be recorded occurs more quickly. In this case, the next recording takes place more quickly than in the case of a constant phase, and the starting point 41 of the striking of the electron beam of the electron gun 6 is schematically changed from FIG. 3 in the case of a slice recording n to a starting point 41 of a slice recording n+1 for example as shown in FIG. 4. In the subsequent slice recordings n+x of the object 27, in which the latter is usually shifted in the direction of the image plane, the starting point 41 is accordingly changed along the anode arc 14. It is thus ensured that similar movement states of the object 27 are always recorded for each slice image. In other words, the starting point 41 of the source trajectory 40 can be changed as a function of the movement state of the object 27.

Here, despite the change in the starting point 41, a short recording time or scanning time is maintained on account of the use of the short circle segments, in which the electron beam migrates along only part of the full circle, as shown in particular in FIGS. 3 and 4.

As described above, slice images with little movement are recorded, and furthermore these slice images are recorded with regard to the similarity of their movement state or phase with a changed starting point 41 on the anode arc 14, so that a three-dimensional image of high quality is obtained from the slice images of the individual X-ray recordings. The three-dimensional image of the object 27 then preferably consists of slice images of the object 27 which are recorded with little movement and exhibit a similar movement state.

The invention claimed is:

1. An electron computer tomography method, comprising:
generating X-ray radiation by deflecting an electron beam onto an anode arc;
wherein the X-ray radiation leaves the anode arc in the form of a fan-shaped beam having a source trajectory in the form of a circle segment around a moving object;
wherein the X-ray radiation passes through the moving object, which is located in a volume of interest, and is detected by a detector;
wherein a starting point of the source trajectory corresponds to a point on the anode arc where only a sub-portion of the volume of interest is irradiated and the moving object is entirely located within the sub-portion of the volume of interest.

2. An electron computer tomography method as claimed in claim 1, in which the starting point of the source trajectory is a function of a movement state of the object.

3. An electron computer tomography method as claimed in claim 1, in which the starting point of the source trajectory is determined on the basis of results of an electrocardiogram of the object.

4. An electron computer tomography method as claimed in claim 1, in which the starting point of the source trajectory is a function of a vertical position of the object.

5. An electron computer tomography method as claimed in claim 1, in which the circle segment of the source trajectory is less than 220°.

6. An electron computer tomography method as claimed in claim 1, in which a filtered back-projection is carried out in order to reconstruct the image.

7. An electron computer tomography method as claimed in claim 1, in which reconstructed images of different movement states of the object are compared and similar images are selected in order to create an overall image of the object.

8. An electron computer tomography method as claimed in claim 7, in which a mean absolute difference method is used to compare the movement states of the object.

9. An electron computer tomography method as claimed in claim 7, in which a cross-correlation method is used to compare the movement states of the object.

10. An electron computer tomography method as claimed in claim 7, in which the reconstructed images for comparing different movement states are images of slices of the object.

11. An electron computer tomograph, comprising:
    an electron gun;
    a focusing coil;
    a curvature coil;
    an anode arc for generating an X-ray beam by being struck by an electron beam of the electron gun; and
    a detector device for detecting X-ray radiation transmitted through a volume;
    wherein said X-ray radiation includes a source trajectory in the form of a circle segment at the anode arc and a starting point of the source trajectory corresponds to a point on the anode arc where only a sub-portion of the volume is irradiated and a moving object is entirely located within the sub-portion of the volume.

12. The electron computer tomography method as claimed in claim 1, wherein a stopping point of the source trajectory corresponds to a point where only the sub-portion of the volume is irradiated and the moving object is entirely located within the sub-region of the volume.

13. The electron computer tomography method as claimed in claim 12, wherein the starting and stopping points are different points on the anode arc.

14. The electron computer tomography method as claimed in claim 12, wherein the starting and stopping points of the source trajectory is a function of a movement state of the object.

15. The electron computer tomography method as claimed in claim 12, wherein the starting and stopping points of the source trajectory are determined on the basis of results of an electrocardiogram of the object.

16. The electron computer tomography method as claimed in claim 12, wherein the starting and stopping points of the source trajectory is a function of a vertical position of the object.

17. The electron computer tomograph as claimed in claim 11, wherein a stopping point of the source trajectory corresponds to a point where only the sub-portion of the volume is irradiated and the moving object is entirely located within the sub-region of the volume.

18. The electron computer tomograph as claimed in claim 17, wherein the starting and stopping points are different points on the anode arc.

19. The electron computer tomograph as claimed in claim 11, wherein the starting point of the source trajectory is a function of a movement state of the object.

20. The electron computer tomograph as claimed in claim 11, wherein the starting point of the source trajectory is a function of the vertical position of the object.

* * * * *